US006617460B1

(12) United States Patent
Anderson et al.

(10) Patent No.: US 6,617,460 B1
(45) Date of Patent: Sep. 9, 2003

(54) PROCESS FOR PREPARING TOLUENESULFINATES

(75) Inventors: Benjamin Alan Anderson, Zionsville, IN (US); Nancy Kay Harn, Zionsville, IN (US); Richard Duane Miller, Pittsboro, IN (US); Edward Francis Plocharczyk, Zionsville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/351,642

(22) Filed: Jan. 24, 2003

Related U.S. Application Data

(62) Division of application No. 09/787,586, filed as application No. PCT/US99/08323 on Apr. 15, 1999.
(60) Provisional application No. 60/103,603, filed on Oct. 9, 1998.

(51) Int. Cl.$^7$ .................... C07D 271/02; C07D 277/22; C07D 413/04; C07D 417/04
(52) U.S. Cl. ................. 548/131; 548/143; 548/203; 548/214; 548/314.7
(58) Field of Search ................................ 548/131, 143, 548/203, 214, 314.7

(56) References Cited

PUBLICATIONS

M. Kobayashi, et al, Organic Sulfur Compounds. VI. The Reactions of Arylsulfinic Acids with Alkyl Chlorocarbonates. Bull. Chem. Soc. Jpn., Nov. 1965, vol. 39, No. 6, pp. 1292–1296.

Harpp, et al., Synthesis and Properties of N–(Alkyl– and arylsulfinyl)phthalimides, A New Class of Sulfinyl–Transfer Reagents, J. Org. Chem., Jun. 1973, vol. 38, No. 25, pp. 4328–4334.

Mochizuki, et al., Sulfonylation and Phosphinylation of Olefinic Compounds with Radical Species Generated by the Oxidation of Sodium Sulfinates and Diphenylphosphine Oxide, Bull. Chem. Soc. Jpn., 1996, vol. 69, pp. 2317–2325.

Ishibashi, et al., A New General Entry to 4–Substituted Indoles, Tetrahedron Letters, 1993, vol. 34, No. 3, pp. 489–492.

Ishibashi, et al., Convenient Synthesis of 4–Alkyl, Alenyl, and Alkynyl Substituted N–(Phenylsulfonyl) indoles, Chem. Pharm. Bull., May 1994, vol. 42, No. 10, pp. 2150–2153.

M. Aso, et al., J. Org. Chem., vol. 58, No. 15, 1993, pp. 3960–3968; XP002179793.

A. Wada, et al., Chem. Pharm. Bull., vol. 42, No. 2, 1994, pp. 416–418; XP002179794.

W.A. Remers, et al., J. Org. Chem., vol. 36, No. 9, 1971, pp. 1232–1240; XP002082911.

F.S. El–Feraly, et al., Can. J. Chem., vol. 63, 1985, pp. 2232–2236; XP001024805.

*Primary Examiner*—Joseph K. McKane
*Assistant Examiner*—Golam M. M. Shameem
(74) *Attorney, Agent, or Firm*—Francis O. Ginah

(57) ABSTRACT

A process for preparing novel compounds useful in the preparation of 1H-indole-3-glyoxamides.

3 Claims, No Drawings

PROCESS FOR PREPARING TOLUENESULFINATES

This application is a divisional of 09/787,586 Mar. 19, 2000 which is a 371 of PCT/US99/08,323 Apr. 15, 1999 which clasims benefit of 60/103,603 Oct. 9, 1998.

This invention relates to a process for preparing certain 1H-indole-3-glyoxamides useful for inhibiting sPLA$_2$ mediated release of fatty acids for conditions such as septic shock and intermediates useful in the preparation of such compounds.

Certain 1H-indole-3-glyoxamides are known to be potent and selective inhibitors of mammalian sPLA$_2$ useful for treating diseases, such as septic shock, adult respiratory distress syndrome, pancreatitis, trauma, bronchial asthma, allergic rhinitis, rheumatoid arthritis and related sPLA$_2$ induced diseases. EPO publication No. 0675110, for example, discloses such compounds.

Various patents and publications describe processes for making these compounds using 4-hydroxy indole intermediates.

The article, "Recherches en serie indolique. VI sur tryptamines substituees", by Marc Julia, Jean Igolen and Hanne Igolen, *Bull. Soc. Chim. France*, 1962, pp. 1060–1068, describes certain indole-3-glyoxylamides and their conversion to tryptamine derivatives.

The article, "2-Aryl-3-Indoleglyoxylamides (FGIN-1): A New Class of Potent and Specific Ligands for the Mitochondrial DBI Receptor (MDR)" by E. Romeo, et al., *The Journal of Pharmacology and Experimental Therapeutics*, Vol. 262, No. 3, (pp. 971–978) describes certain 2-aryl-3-indolglyoxylamides having research applications in mammalian central nervous systems.

The abstract, "Fragmentation of N-benzylindoles in Mass Spectrometry"; Chemical Abstracts, Vol. 67, 1967, 73028h, reports various benzyl substituted phenols including those having glyoxylamide groups at the 3 position of the indole nucleus.

U.S. Pat. No. 3,449,363 describes trifluoromethylindoles having glyoxylamide groups at the 3 position of the indole nucleus.

U.S. Pat. No. 3,351,630 describes alpha-substituted 3-indolyl acetic acid compounds and their preparation inclusive of glyoxylamide intermediates.

U.S. Pat. No. 2,825,734 describes the preparation of 3-(2-amino-1-hydroxyethyl)indoles using 3-indoleglyoxylamide intermediates such as 1-phenethyl-2-ethyl-6-carboxy-N-propyl-3-indoleglyoxylamide (see, Example 30).

U.S. Pat. No. 4,397,850 prepares isoxazolyl indolamines using glyoxylamide indoles as intermediates. U.S. Pat. No. 3,801,594 describes analgesics prepared using 3-indoleglyoxylamide intermediates.

The article, "No. 565.—Inhibiteurs d'enzymes. XII.—Preparation de (propargylamino-2 ethyl)-3 indoles" by A. Alemanhy, E. Fernandez Alvarez, O. Nieto Lopey and M. E. Rubio Herraez; *Bulletin De La Societe Chimigue De France*, 1974, No. 12, pp. 2883–2888, describes various indolyl-3 glyoxamides which are hydrogen substituted on the 6-membered ring of the indole nucleus.

The article "Indol-Umlagerung von 1-Diphenylamino-2, 3-dihydro-2,3-pyrrolidonen" by Gert Kollenz and Christa Labes; *Liebigs Ann. Chem.*, 1975, pp. 1979–1983, describes phenyl substituted 3-glyoxylamides.

Many of these processes employ a 4-hydroxy indole intermediate. For example U.S. Pat. No. 5,654,326 U.S., herein incorporated by reference in its entirety, discloses a process for preparing 4-substituted-1H-indole-3-glyoxamide derivatives comprising reacting an appropriately substituted 4-methoxyindole (prepared as described by Clark, R. D. et al., *Synthesis*, 1991, pp 871–878, the disclosures of which are herein incorporated by reference) with sodium hydride in dimethylformamide at room temperature (20–25° C.) then treating with arylmethyl halide at ambient temperatures to give the 1-arylmethylindole which is O-demethylated using boron tribromide in methylene chloride (Tsung-Ying Shem and Charles A. Winter, *Adv. Drug Res.*, 1977, 12, 176, the disclosure of which is incorporated by reference) to give the 4-hydroxyindole. Alkylation of the hydroxy indole is achieved with an alpha bromoalkanoic acid ester in dimethylformamide using sodium hydride as a base. Conversion to the glyoxamide is achieved by reacting the -[(indol-4-yl)oxy]alkanoic acid ester first with oxalyl chloride, then with ammonia, followed by hydrolysis with sodium hydroxide in methanol.

The process for preparing 4-substituted-1H-indole-3-glyoxamide derivatives, as set forth above, has utility. However, this process uses expensive reagents and environmentally hazardous organic solvents, produces furan containing by-products and results in a relatively low yield of desired product.

In an alternate preparation, an appropriately substituted propronylacetate is halogenated with sulfuryl chloride. The halogenated intermediate is hydrolyzed and decarboxylated by treatment with hydrochloric acid then reacted with an appropriately substituted cyclohexane dione. Treatment of the alkylated dione with an appropriate amine affords a 4-keto-indole which is oxidized by refluxing in a high-boiling polar hydrocarbon solvent such as carbitol in the presence of a catalyst, such as palladium on carbon, to prepare the 4-hydroxyindole which may then be alkylated and converted to the desired glyoxamide as described above.

This process however is limited by the required high temperature oxidation and requires recovery of a precious metal catalyst.

While the methods described above for preparing the 4-hydroxy indole intermediate are satisfactory, a more efficient transformation is desirable.

The process of the present invention employs a sulfinylation step.

In general, sulfinylation reactions employ the use of hydride bases which cause a delayed onset exotherm and the evolution of gas. Such process conditions are undesirable in a commercial setting.

Applicants have discovered a process for preparing sulfinylated intermediates which is not associated with a delayed onset exotherm and avoids the foaming associated with the liberation of gas.

Patai, *The Chemistry of Sulfinic Acids, Esters and Their Derivatives*, John Wiley and Sons, 1990, p. 11, teaches a synthesis of sulfinic esters and their salts using a variety of activating agents.

In yet another aspect of the invention, applicants have discovered a commercially viable process for preparing sulfinic esters which result in higher yields, avoids the production of sulfur containing byproducts, particularly sulfones and employs inexpensive reagents.

The present invention provides an improved process for preparing 1H-indole-3-glyoxamides. The process of the present invention can be performed with inexpensive, readily available, reagents under milder conditions and resulting in better overall yield while avoiding the production of furan byproducts. In addition, the present process allows for transformation with a wider variety of substituents on the indole platform. Other objects, features and advantages of the present invention will become apparent from the subsequent description and the appended claims.

The present invention provides a process for preparing a compound of the formula I or a pharmaceutically acceptable salt or prodrug derivative thereof;

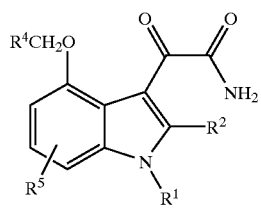

wherein:

$R^1$ is selected from the group consisting of $C_7$–$C_{20}$ alkyl;

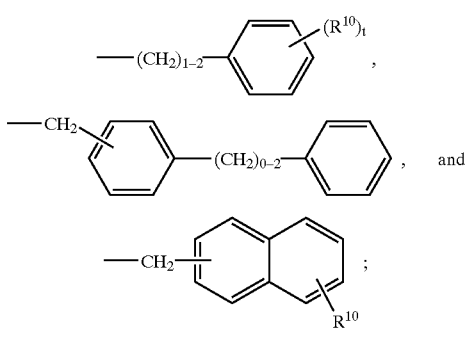

wherein;

$R^{10}$ is selected from the group consisting of halo, —$C_1$–$C_{10}$ alkyl, —$C_1$–$C_{10}$(alkoxy), —S—($C_1$–$C_{10}$) alkyl and halo($C_1$–$C_{10}$)alkyl, and t is an integer from 0 to 5 both inclusive;

$R^2$ is selected from the group consisting of hydrogen, halo, —$C_1$–$C_3$(alkyl), —$C_3$–$C_4$(cycloalkyl), —$C_3$–$C_4$ (cyclo-alkenyl), —O($C_1$–$C_2$) alkyl, —S($C_1$–$C_2$) alkyl, aryl, aryloxy, and HET;

R4 is selected from the group consisting of —$CO_2H$, —$SO_3H$, and —$P(O)(OH)_2$ or salt or prodrug derivatives thereof; and $R^5$ is selected from the group consisting of hydrogen, —($C_1$–$C_6$)alkyl, —($C_1$–$C_6$)alkoxy, halo($C_1$–$C_6$) alkoxy, halo($C_2$–$C_6$)alkyl, bromo, chloro, fluoro, iodo and aryl;

which process comprises the steps of:

a) halogenating a compound of formula X

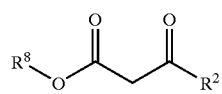

where $R^8$ is ($C_1$–$C_6$)alkyl, aryl or HET;

with $SO_2Cl_2$ to form a compound of formula IX

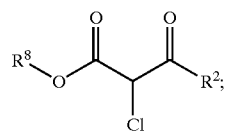

b) hydrolyzing and decarboxylating a compound of formula IX

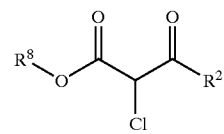

to form a compound of formula VIII

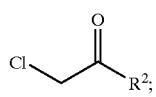

c) alkylating a compound of formula VII

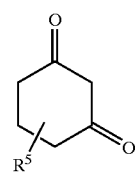

with a compound of formula VIII

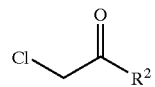

to form a compound of formula VI

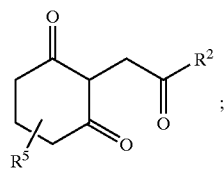

d) aminating and dehydrating a compound of formula VI

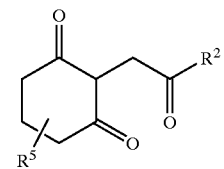

with an amine of the formula R¹NH₂ in the presence of a solvent that forms an azeotrope with water to form a compound of formula V

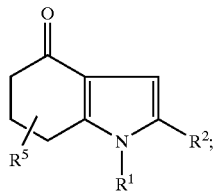

V e) oxidizing a compound of formula V

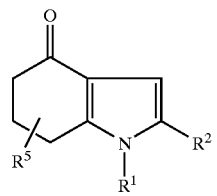

V by heating with a base and a compound of the formula RSOX where R is -(C₁–C₆)alkyl, aryl, or substituted aryl and X is -(C₁–C₆)alkoxy, halo or —OCO₂(C₁–C₆)alkyl to form a compound of formula IV

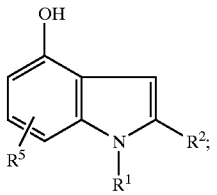

IV f) alkylating a compound of the formula IV

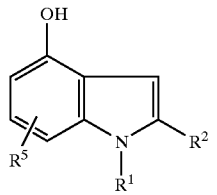

IV with an alkylating agent of the formula XCH₂R⁴ᵃ where X is a leaving group and R⁴ᵃ is —CO₂R⁴ᵇ, —SO₃R⁴ᵇ, —P(O)(OR⁴ᵇ)₂, or —P(O)(OR⁴ᵇ)H, where R⁴ᵇ is an acid protecting group, to form a compound of formula III

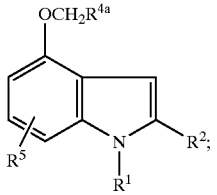

III g) reacting a compound of formula III

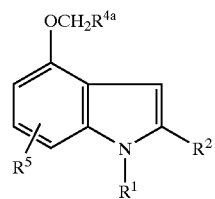

III with oxalyl chloride and ammonia to form a compound of formula II

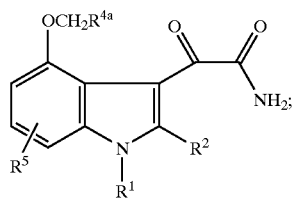

II h) optionally hydrolyzing a compound of formula II

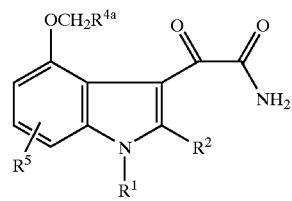

II to form a compound of formula I; and i) optionally salifying a compound of formula I.

In another embodiment of the invention is provided a process for preparing a compound of formula I comprising the steps of:

a) oxidizing a compound of the formula V

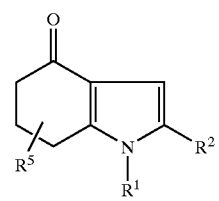

V by heating with a base and a compound of the formula RSOX where R is —(C₁–C₆)alkyl, aryl, or substituted aryl and X is —(C₁–C₆)alkoxy, halo or —OCO₂(C₁–C₆)alkyl to form a compound of formula IV

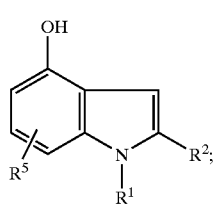

IV b) alkylating a compound of the formula IV

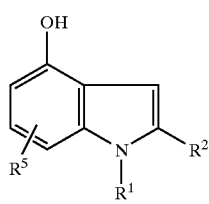

IV with an alkylating agent of the formula $XCH_2R^{4a}$ where X is a leaving group and $R^{4a}$ is $—CO_2R^{4b}$, $—SO_3R^{4b}$, $—P(O)(OR^{4b})_2$, or $—P(O)(OR^{4b})H$, where $R^{4b}$ is an acid protecting group, to form a compound of formula III

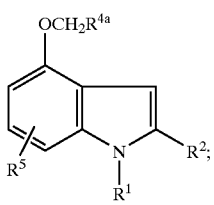

III c) reacting a compound of formula III

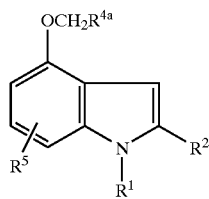

III with oxalyl chloride and ammonia to form a compound of formula II

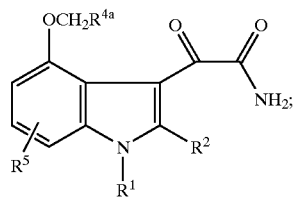

II and
d) optionally hydrolyzing a compound of formula II

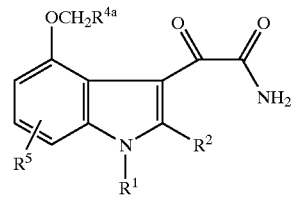

II to form a compound of formula I; and
e) optionally salifying a compound of formula I.

In an alternate embodiment of the invention is provided a process for preparing a compound of formula I comprising the steps of:

a) oxidizing a compound of the formula V

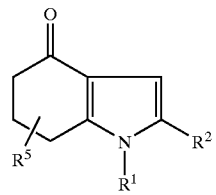

V by treating with a base and a compound of the formula RSOX where R is $—(C_1–C_6)$alkyl, aryl, or substituted aryl and X is $—(C_1–C_6)$alkoxy, halo or $—OCO_2(C_1–C_6)$alkyl to form a compound of formula VI

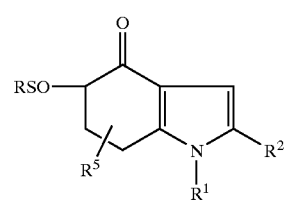

$V^1$ heating a component of formula $V^1$ to form a compound of formula IV

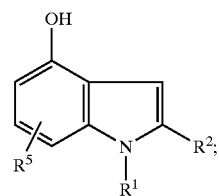

IV b) alkylating a compound of the formula IV

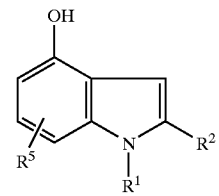

IV with an alkylating agent of the formula $XCH_2R^{4a}$ where X is a leaving group and $R^{4a}$ is $—CO_2R^{4b}$, $—SO_3R^{4b}$, $—P(O)(OR^{4b})_2$, or $—P(O)(OR^{4b})H$, where $R^{4b}$ is an acid protecting group, to form a compound of formula III

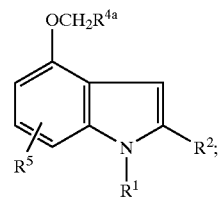

III c) reacting a compound of formula III

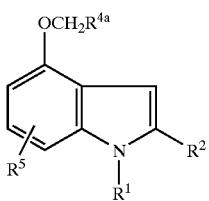

III with oxalyl chloride and ammonia to form a compound of formula II

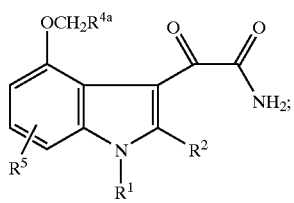

II and
d) optionally hydrolyzing a compound of formula II

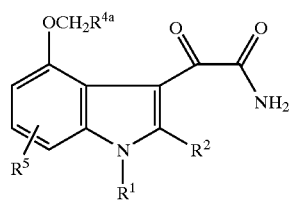

II to form a compound of formula I; and
The present invention provides, in addition, novel intermediates of the formula $V^1$

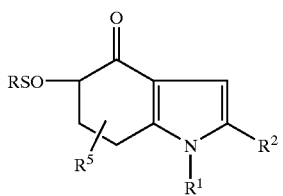

$V^1$ where $R^1$, $R^2$ and $R^5$ are as defined above and R is —$(C_1-C_6)$alkyl, aryl or substituted aryl. Such compounds are useful in the process of preparing compounds of formula I.

In yet another aspect, the present invention provides a process for preparing compounds of the formula RSOX where R is —$(C_1-C_6)$alkyl, aryl or substituted aryl and X is —$(C_1-C_6)$alkoxy; comprising treating a compound of the formula

RSOM where R is —$(C_1-C_6)$alkyl, aryl or substituted aryl and H is an alkali metal; with an acid and an alcohol of the formula —$(C_1-C_2)$alkoxy.

The compounds of the invention employ certain defining terms as follows:

As used herein, the term, "alkyl" by itself or as part of another substituent means, unless otherwise defined, a straight or branched chain monovalent hydrocarbon radical such as methyl, ethyl, n-propyl, isopropyl, n-butyl, tertiary butyl, isobutyl, sec-butyl, tert-butyl, n-pentyl, isopentyl, neopentyl, heptyl, hexyl, octyl, nonyl, decyl, and the like.

The term "$(C_1-C_{10})$ alkoxy", as used herein, denotes a group such as methoxy, ethoxy, n-propoxy, isopropoxy, n-butoxy, t-butoxy, n-pentoxy, isopentoxy, neopentoxyl, heptoxy, hexoxy, octoxy, nonoxy, decoxy and like groups, attached to the remainder of the molecule by the oxygen atom.

The term "$(C_3-C_4)$ cycloalkyl" includes cyclopropyl, and cyclobutyl groups

The term "C3–C4 cycloalkenyl" includes a cyclopropenyl or cyclobutenyl ring having a double bond at the 1- or 2-position.

The term "halo" means fluoro, chloro, bromo or iodo.

The term "halo$(C_1-C_{10})$alkyl" means a $(C_1-C_{10})$alkyl group, substituted with from 1 to 3 halo atoms, attached to the remainder of the molecule by the alkyl group. The term halo$(C_1-C_{10})$alkyl includes the term halo$(C_2-C_6)$alkyl.

The term "halo$(C_1-C_6)$alkoxy" means a halo-substituted alkoxy group which group is attached to the remainder of the molecule at the oxygen of the alkoxy.

The term "aryl" means a group having the ring structure characteristic of benzene, pentalene, indene, naphthalene, azulene, heptalene, phenanthrene, anthracene,etc. The aryl group may be optionally substituted with 1 to 3 substituents selected from the group consisting of $(C_1-C_6)$alkyl (preferably methyl), $(C_1-C_6)$alkoxy or halo (preferable fluorine or chlorine).

The term "aryloxy" means an aryl group attached to the remainder of the molecule by an oxygen linker.

The term "leaving group" means a substituent with an unshared electron pair that departs from the substrate in a nucleophilic substitution reaction. The term "leaving group" includes halo, sulfonate, acetate and the like.

The term HET includes pyridine, pyrazine, pyrimidine, pyridazine, pyrrole, pyrazole, furan, thiophene, thiazole, isothiazole, oxadiazole, thiadiazole, imidazole, triazole and tetrazole. The heterocyclic ring can be attached to the remainder of the molecule by any carbon in the heterocyclic ring.

The salts of the compounds of formula I are an additional aspect of the invention. In those instances where the compounds of the invention possess acidic functional groups various salts may be formed which are more water soluble and physiologically suitable than the parent compound. Representative pharmaceutically acceptable salts include but are not limited to the alkali and alkaline earth salts such as lithium, sodium, potassium, calcium, magnesium, aluminum and the like. Salts are conveniently prepared from the free acid by treating the acid in solution with a base or by exposing the acid to an ion exchange resin.

Included within the definition of pharmaceutically acceptable salts are the relatively non-toxic, inorganic and organic base addition salts of compounds of the present invention, for example, ammonium, quaternary ammonium, and amine cations, derived from nitrogenous bases of sufficient basicity to form salts with the compounds of this invention (see, for example, S. M. Berge, et al., "Pharmaceutical Salts," *J. Phar. Sci.*, 66: 1–19 (1977)).

The term "acid protecting group" is used herein as it is frequently used in synthetic organic chemistry, to refer to a group which will prevent an acid group from participating in a reaction carried out on some other functional group of the molecule, but which can be removed when it is desired to do so. Such groups are discussed by T. W. Greene in chapter 5 of *Protective Groups in Organic Synthesis*, John Wiley and Sons, New York, 1981, incorporated herein by reference in its entirety.

Examples of acid protecting groups includes ester or amide derivatives of the acid group, such as methyl, methoxymethyl, methyl-thiomethyl, tetrahydropyranyl, methoxyethoxymethyl, benzyloxymethyl, phenylaryl, ethyl, 2,2,2-trichloroethyl, 2-methylthioethyl, t-butyl, cyclopentyl, triphenylmethyl, p-bromobenzyl, trimethylsilyl, N,N-dimethyl, pyrrolidinyl, piperidinyl or o-nitroanilide. A preferred acid-protecting group is methyl.

Prodrugs are derivatives of the compounds of the invention which have chemically or metabolically cleavable groups and become by solvolysis or under physiological conditions the compounds of the invention which are pharmaceutically active in vivo. Derivatives of the compounds of this invention have activity in both their acid and base derivative forms, but the acid derivative form often offers advantages of solubility, tissue compatibility, or delayed release in a mammalian organism (see, Bundgard, H., *Design of Prodrugs*, pp. 7–9, 21–24, Elsevier, Amsterdam 1985). Prodrugs include acid derivatives, such as, esters prepared by reaction of the parent acidic compound with a suitable alcohol, or amides prepared by reaction of the parent acid compound with a suitable amine. Simple aliphatic esters (e.g., methyl, ethyl, propyl, isopropyl, butyl, sec-butyl, tert-butyl) or aromatic esters derived from acidic groups pendent on the compounds of this invention are preferred prodrugs. Other preferred esters include morpholinoethyloxy, diethylglycolamide and diethylaminocarbonylmethoxy.

In some cases it is desirable to prepare double ester type prodrugs such as (acyloxy) alkyl esters or ((alkoxycarbonyl)oxy)alkyl esters.

A preferred group of compounds of formula I prepared by the process of the instant invention are those wherein:
$R^1$ is

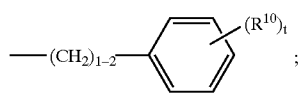

Where $R^{10}$ is selected from the group consisting of halo, —$C_1$–$C_{10}$ alkyl, —$C_1$–$C_{10}$(alkoxy), —S—($C_1$–$C_{10}$) alkyl and halo($C_1$–$C_{10}$)alkyl, and t is an integer from 0 to 5 both inclusive;
$R^2$ is halo, cyclopropyl, methyl, ethyl, propyl, O-methyl or S-methyl;
$R^4$ is —$CO_2H$; and
$R^5$, $R^6$ and $R^7$ are H.
Preferred compounds of formula $V^1$ are those wherein
R is aryl
where $R^{10}$ is selected from the group consisting of halo, —($C_1$–$C_{10}$)alkyl, —($C_1$–$C_{10}$)alkoxy, —S($C_1$–$C_{10}$) alkyl and halo ($C_1$–$C_{10}$)alkyl, and t is an integer from 0 to 5;
$R^2$ is selected from the group consisting of halo, cyclopropyl, methyl, ethyl, propyl, O-methyl and S-methyl; and
$R^5$ is H.
Even more preferred are compounds of formula $V^1$ wherein R is phenyl or tolyl;
$R^1$ is

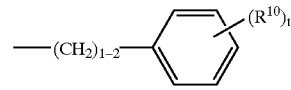

R10 is selected from the group consisting of halo, —($C_1$–$C_4$)alkyl, —($C_1$–$C_4$)alkoxy, —S($C_1$–$C_4$)alkyl and halo ($C_1$–$C_4$)alkyl, and t is 2;
$R^2$ is methyl, ethyl or propyl; and
$R^5$ is H.
Preferred substituent groups of compounds of formula $V^1$ include the following:
(a) $R^1$ is

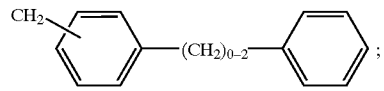

(b) $R^1$ is

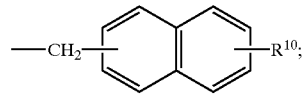

(c) $R^1$ is —($C_1$–$C_{13}$)alkyl;
(d) $R^{10}$ is selected from the group consisting of —($C_1$–$C_6$) alkyl and —($C_1$–$C_6$)alkoxy;
(e) $R^{10}$ is selected from the group consisting of —S($C_1$–$C_6$)alkyl and halo ($C_1$–$C_6$)alkyl;
(f) t is an integer from 0 to 3, both inclusive;
(g) $R^2$ is selected from the group consisting of hydrogen, halo, —($C_1$–$C_3$)alkyl, and —O($C_1$–$C_6$)alkyl;
(h) $R^2$ is selected from the group consisting of —O($C_1$–$C_2$)alkyl and —S($C_1$–$C_2$)alkyl;
(i) $R^2$ is selected from the group consisting of aryl and aryloxy;
(j) $R^2$ is HET;
(k) $R^5$ is selected from the group consisting of hydrogen, ($C_1$–$C_6$)alkyl and ($C_1$–$C_6$)alkoxy;
(l) $R^5$ is selected from the group consisting of halo ($C_1$–$C_6$)alkoxy and halo($C_2$–$C_6$)alkyl;
(m) $R^5$ is selected from the group consisting of bromo, chloro, fluoro and codo;
(n) $R^5$ is aryl.
Compounds which can be made by the process of the instant invention include:
((3-(2-amino-1,2-dioxyethyl)-2-methyl-1-(phenylmethyl)-1H-indol-4-yl)oxy)acetic acid;
dl-2-((3-(2-amino-1,2-dioxyethyl)-2-methyl-1-(phenylmethyl)-1H-indol-4-yl)oxy)propanoic acid;
((3-(2-amino-1,2-dioxyethyl)-1-((1,1'-biphenyl)-2-ylmethyl)-2-methyl-1H-indol-4-yl)oxy)acetic acid;
((3-(2-amino-1,2-dioxyethyl)-1-((1,1'-biphenyl)-3-ylmethyl)-2-methyl-1H-indol-4-yl)oxy)acetic acid;
((3-(2-amino-1,2-dioxyethyl)-1-((1,1'-biphenyl)-4-ylmethyl)-2-methyl-1H-indol-4-yl)oxy)acetic acid;
((3-(2-amino-1,2-dioxyethyl)-1-((2,6-dichlorophenyl)methyl)-2-methyl-1H-indol-4-yl)oxy)acetic acid;
((3-(2-amino-1,2-dioxyethyl)-1-(4-fluorophenyl)methyl)-2-methyl-1H-indol-4-yl)oxy)acetic acid;

((3-(2-amino-1,2-dioxyethyl)-2-methyl-1-((naphthalenyl)
methyl)-1H-indol-4-yl)oxy)acetic acid;
((3-(2-amino-1,2-dioxyethyl)-2-ethyl-1-(phenylmethyl)-
1H-indol-4-yl)oxy)acetic acid;
((3-(2-amino-1,2-dioxyethyl)-1-((3-chlorophenylmethyl)-2-
ethyl-1H-indol-4-yl)oxy)acetic acid;
((3-(2-amino-1,2-dioxyethyl)-1-((1,1'biphenyl)-2-
ylmethyl)-2-ethyl-1H-indol-4-yl)oxy)acetic acid;
((3-(2-amino-1,2-dioxyethyl)-1-((1,1'-biphenyl)-2-
ylmethyl)-2-propyl-1H-indol-4-yl)oxy)acetic acid;
((3-(2-amino-1,2-dioxyethyl)-2-cyclopropyl-1-
(phenylmethyl)-1H-indol-4-yl)oxy)acetic acid;
((3-(2-amino-1,2-dioxyethyl)-1-((1,1'biphenyl)-2-
ylmethyl)-2-cyclopropyl-1H-indol-4-yl)oxy)acetic acid;
4-((3-(2-amino-1,2-dioxyethyl)-2-ethyl-1-(phenylmethyl)-
1H-indol-4-yl)oxy)butanoic acid;
((3-(2-amino-1,2-dioxyethyl)-2-ethyl-1-(phenylmethyl)-
1H-indol-4-yl)oxyacetic acid;
((-3-(2-amino-1,2-dioxyethyl1-2-ethyl-6-methyl-1-
(phenylmethyl)-1H-indol-4-yl)oxy)acetic acid;
((-3-(2-amino-1,2-dioxyethyl)-2,6-dimethyl-1-
(phenylmethyl)-1H-indol-4-yl)oxy)acetic acid;
((3-(2-amino-1,2-dioxyethyl)-2-methyl-1-(phenylmethyl)-
1H-indol-4-yl)oxy)acetic acid;
((3-(2-amino-1,2-dioxyethyl)-6-ethyl-2-methyl-1-
(phenylmethyl)-1H-indol-4-yl)oxy)acetic acid;
((3-(2-amino-1,2-dioxyethyl)-2,6-diethyl-1-
(phenylmethyl)-1H-indol-4-yl)oxy)acetic acid;
((3-(2-amino-1,2-dioxyethyl)-2-methyl-6-phenoxy-1-
(phenylmethyl)-1H-indol-4-yl)oxy)acetic acid;
((3-(aminooxoacetyl)-2-ethyl-6-methyl-1-(phenylmethyl)-
1H-indol-4-yl)oxy)acetic acid; and
((3-(2-amino-1,2-dioxyethyl)-2-ethyl-6-phenoxy-1-
(phenylmethyl)-1H-indol-4-yl)oxy)acetic acid or a phar-
maceutically acceptable salt thereof.

Of these compounds, preferred compounds include:
((3-(2-amino-1,2-dioxyethyl)-2-ethyl-1-(phenylmethyl)-
1H-indol-4-yl)oxyacetic acid;
((-3-(2-amino-1,2-dioxyethyl)-2-ethyl-6-methyl-1-
(phenylmethyl)-1H-indol-4-yl)oxy)acetic acid;
((-3-(2-amino-1,2-dioxyethyl)-2,6-dimethyl-1-
(phenylmethyl)-1H-indol-4-yl)oxy)acetic acid;
((3-(2-amino-1,2-dioxyethyl)-2-methyl-1-(phenylmethyl)-
1H-indol-4-yl)oxy)acetic acid;
((3-(2-amino-1,2-dioxyethyl)-6-ethyl-2-methyl-1-
(phenylmethyl)-1H-indol-4-yl)oxy)acetic acid;
((3-(2-amino-1,2-dioxyethyl)-2,6-diethyl-1-
(phenylmethyl)-1H-indol-4-yl)oxy)acetic acid;
((3-(2-amino-1,2-dioxyethyl)-2-methyl-6-phenoxy-1-
(phenylmethyl)-1H-indol-4-yl)oxy)acetic acid;
((3-(aminooxoacetyl)-2-ethyl-6-methyl-1-(phenylmethyl)-
1H-indol-4-yl)oxy)acetic acid; and
((3-(2-amino-1,2-dioxyethyl)-2-ethyl-6-phenoxy-1-
(phenylmethyl)-1H-indol-4-yl)oxy)acetic acid or a phar-
maceutically acceptable salt thereof.

Of these compounds even more preferred are:
((3-(2-amino-1,2-dioxyethyl)-2-methyl-1-(phenylmethyl)-
1H-indol-4-yl)oxy)acetic acid and ((3-(2-amino-1,2-
dioxyethyl)-2-ethyl-1-(phenylmethyl)-1H-indol-4-yl)
oxyacetic acid.

The most preferred compound which can be prepared by
the instant process is ((3-(2-amino-1,2-dioxyethyl)-2-ethyl-
1-(phenylmethyl)-1H-indol-4-yl)oxyacetic acid or a phar-
maceutically acceptable salt thereof.

The process of the present invention provides an
improved method for synthesizing the compounds of for-
mula I using inexpensive, readily available reagents as
shown in Scheme I as follows.

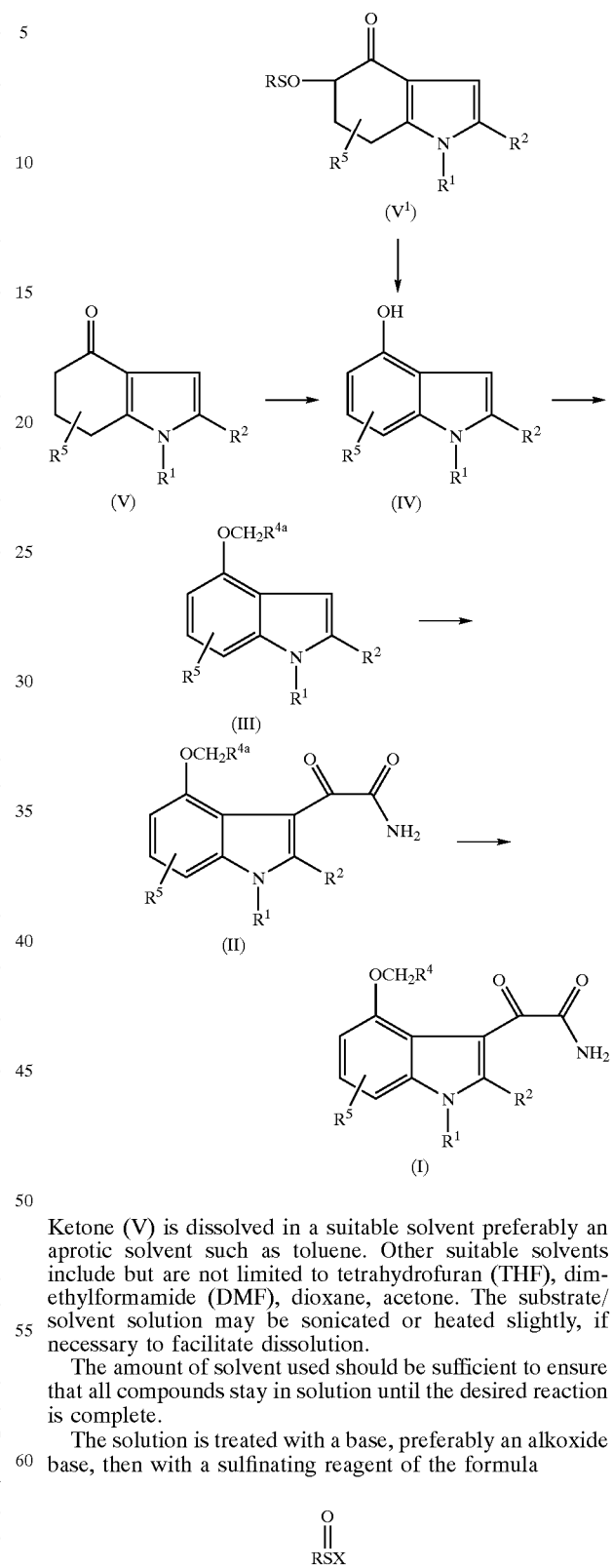

Ketone (V) is dissolved in a suitable solvent preferably an
aprotic solvent such as toluene. Other suitable solvents
include but are not limited to tetrahydrofuran (THF), dim-
ethylformamide (DMF), dioxane, acetone. The substrate/
solvent solution may be sonicated or heated slightly, if
necessary to facilitate dissolution.

The amount of solvent used should be sufficient to ensure
that all compounds stay in solution until the desired reaction
is complete.

The solution is treated with a base, preferably an alkoxide
base, then with a sulfinating reagent of the formula

where R is —$(C_1-C_6)$alkyl, aryl or substituted aryl and X is
$(C_1-C_6)$alkoxy, halo or —$OCO_2(C_1-C_6)$alkyl. The sulfinating reagent may be prepared according to the procedure of J. W. Wilt et al., *J. Org. Chem*, 1967, 32, 2097. Preferred sulfinating agents include methyl p-tolyl sulfinate, methylbenzene sulfinate or p-toluylsulfinic isobutyric anhydride. Preferred alkoxide bases include methoxide or ethoxide bases of sodium, potassium or lithium. Potassium methoxide is especially preferred. Other suitable bases include but are not limited to sodium hydride, or LDA. Generally, from about 0.75 to 10 equivalents of base relative to the starting material is employed; preferable from about 1 to about 3 equivalents; most preferably about 2 equivalents. The reaction may be conducted at temperatures from about 15° C. to reflux, and is substantially complete in from one to 24 hours. Intermediate VI can be isolated by conducting the reaction at temperatures of from 15° C. to 50° C., preferably at from 25° C. to 40° C., more preferably at 30° C. The conversion of intermediate V to VI will proceed rapidly if the reaction is run at temperatures of from 60° C. to reflux, preferably from 75° C. to 85° C. more preferably at The amount of sulfinating reagent is not critical, however, the reaction is best accomplished using a molar equivalent or excess relative to the pyrrole starting material (V).

In an alternate preparation of $V^1$, a sulfinating reagent is replaced with a disulfide compound of the formula $R^{20}SSR^{20}$ where $R^{20}$ is —$(C_1$–$C_6)$alkyl, alkyl or aryl, to prepare on oxidation of the XX is then be readily achieved using an appropriate oxidizing reagent such as hydrogen peroxide or m-chloroperbenzoic acid.

Indole (IV) may then be readily alkylated with an alkylating agent of the formula $XCH_2R^{4a}$ where X is a suitable leaving group and $R^{4a}$ is a protected carboxy, sulfonyl or phosphonyl acid group, preferably protected with an ester group, in the presence of a base. Methyl bromoacetate is a preferred alkylating agent. Suitable bases include potassium carbonate, sodium carbonate, lithium carbonate, cesium carbonate, sodium bicarbonate, potassium bicarbonate or potassium hydroxide. Potassium carbonate is preferred. The amount of alkylating agent is not critical, however, the reaction is best accomplished using a molar excess of alkylating agent relative to the starting material. The reaction is preferably carried out in an organic solvent such as acetone, acetonitrile or dimethylformanide. Other suitable solvents include but are not limited to methanol, toluene, tetrahydrofuran, methyl ethyl ketone, acetonitrile, or t-butyl methylether. The reaction is conducted at temperatures of from about 0° to 100° C., preferably at ambient temperature, and is substantially complete in about 1 to 24 hours depending on the reactants employed and such conditions as reaction temperature.

Optionally, a phase transfer reagent such as tetrabutylammoniumbromide may be employed.

Preparation of glyoxamide II is readily achieved in a two step process by first treating intermediate III with oxalyl chloride at concentrations from about 0.2 to 1.5 mmol, preferably at equimolar concentrations relative to the starting material. Solvents such as methylene chloride, chloroform, trichloroethylene, carbon tetrachloride, ether or toluene are preferred. Temperatures from about −20° C. to ambient temperature are suitable, preferably about −5° C.

In the second step, the solution is treated with ammonia; either bubbled in as a gas or, preferably, using a molar excess of 30% aqueous ammonia. The reaction is typically conducted at temperatures from about −25° C. to 25° C., preferably at about −2° C. to 0° C., and is substantially complete in 10 minutes to an hour.

Hydrolysis of II is achieved using a base such as potassium hydroxide, lithium hydroxide or sodium hydroxide, preferably sodium hydroxide, in a lower alcohol solvent, such as methanol, ethanol, isopropanol, etc., or solvents such as tetrahydrofuran, dioxane and acetone.

Using standard analytical techniques, such as HPLC, the reactions of Scheme I can be monitored to determine when starting materials and intermediates are converted to product.

The intermediates $V^1$ and IV can be isolated. For example, intermediate IV can be isolated by extraction from a solution of IV in a suitable organic solvent, such as toluene, into a solution of a base and a water miscible solvent. The pH of the aqueous layer must initially be greater than 12. The layers are separated and the pH of the aqueous layer is adjusted to a range of from 1 to 12 more preferably 9–11.5 most preferably 11, Intermediate IV is isolated from the aqueous layer, preferably by extraction into an organic solvent in which the intermediate is soluble. Suitable water-miscible solvents include but are not limited to methanol, acetone, isopropanol, acetonitrile, dioxane or tetrahydrofuran. The pH of the aqueous layer must initially be greater than 12. Concentrations of base from about 0.5N to 5N are preferred, more preferably, from about 1.5N to 2.5N. The most preferred concentration of base is 2N. Methanol is preferred. Although the order of addition is not critical, preferably the pH of the aqueous solution containing the intermediate is adjusted after addition of the organic solvent into which the intermediate IV is to be extracted.

Scheme I(a), below, illustrates the two pot procedure, described above, for the preparation of intermediate IV. Intermediate $V^1$ can be isolated and purified using standard chromatographic procedures.

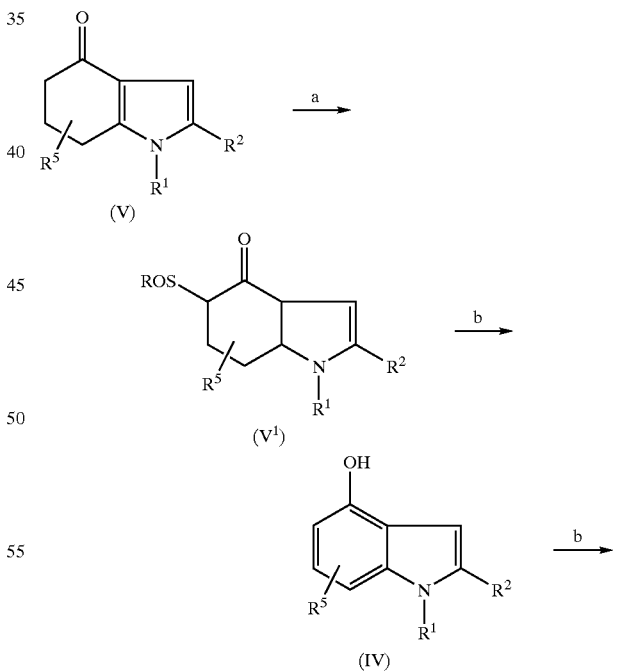

Scheme I (a)

It will be readily appreciated by the skilled artisan that the starting materials for the above procedures are either commercially available or can be readily prepared by known techniques from commercially available starting materials.

Starting material V is prepared according to the following procedure.

Scheme II

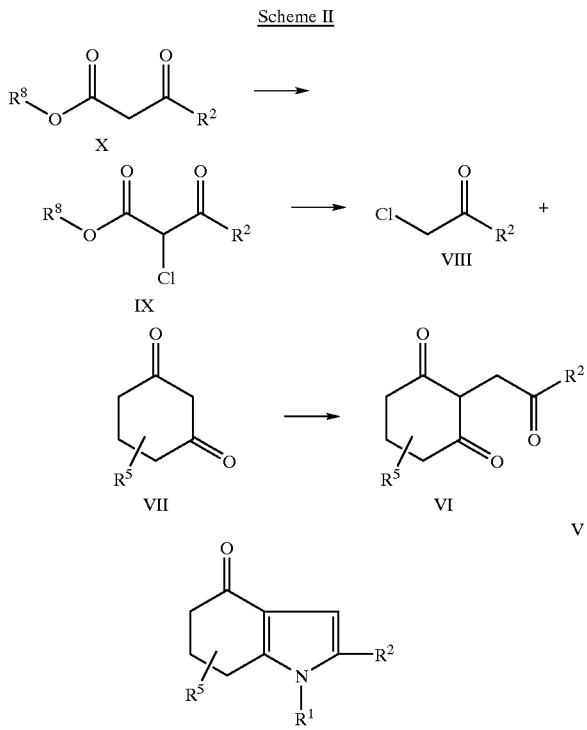

$R^8$ is $(C_1-C_6)$ alkyl or aryl

An appropriately substituted propionylacetate X is first halogenated by treatment with sulfuryl chloride, preferably at equimolar concentrations relative to the starting material, at temperatures of from about 0° C. to 25° C., preferably less than 15° C., to prepare IX.

Hydrolysis and decarboxylation of IX is achieved by refluxing with an aqueous acid, such as hydrochloric acid, for from about 1 to 24 hours. The solution containing the decarboxylated product VIII is neutralized to adjust the pH to about 7.0–7.5, then reacted with cyclohexanedione VII (preferably at equimolar concentrations) and a base, preferably sodium hydroxide, to yield the triketone monohydrate VI as a precipitate which may be purified and isolated, if desired. The reaction is preferably conducted at temperatures of from −20° C. to ambient temperatures and is substantially complete in about 1 to 24 hours.

The above reactions are preferably run as a "one pot" process with the reactants added to the reaction vessel in the order given above. Preferably, the reaction is allowed to proceed without isolating compounds of formula IX or VIII, thus avoiding exposure to these volatile lachrymators.

Preparation of V is achieved by refluxing VI in a high boiling non-polar solvent which forms an azeotrope with water, preferably toluene, with an equimolar quantity of an amine of the formula $R^1NH_2$, where $R^1$ is as defined above.

Solvents with a boiling point of at least 100° C. are preferred, such as toluene, xylene, cymene, benzene, 1,2-dichloroethane or mesitylene, thus eliminating the need for a pressure reactor. Sufficient solvent should be employed to ensure that all compounds stay in solution until the reaction is substantially complete in about 1 to 24 hours.

In a preferred procedure sulfinylating reagents

may be prepared in an acid catalyzed reaction by reacting an appropraite aryl sulfinate of the formula

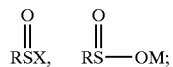

where M is an alkali metal, preferably sodium, and R is —$(C_1-C_6)$alkyl, aryl or substituted aryl, preferably phenyl or tolyl; with an acid, preferably hydrochloric acid. The reaction is preferably conducted at ambient temperatures preferably 15–30° C., more preferably 20–25° C. in the alcohol solvent which corresponds to the desired ester product, preferably methanol. Other suitable solvents include ethanol and isopropanol. In an alternate procedure, the reaction may be run with an equivalent of the desired alcohol in a suitable aprotic solvent such as toluene. More preferably the reaction is run with an excess of alcohol in solvent; most preferably in neat alcohol which corresponds to the desired ester product,

Preferably, the reaction is conducted using a molar excess of acid relative to the sulfinate starting material.

The following examples further illustrate the process of the present invention. The examples also illustrate the preparation of the intermediate compounds of this invention. The examples are illustrative only and not intended to limit the scope of the invention in any way.

Preparation 1

(±) methyl-p-toluenesulfinate

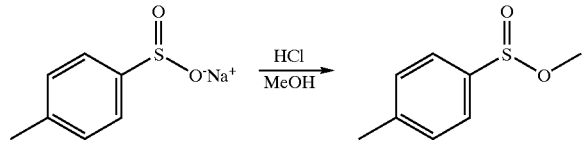

To a 5-liter, 3-neck round bottom flask, was added 2845 mls of methanol (5 volumes) and was bubbled in 165.58 grams (1.4 equivalents, 4.47 gmoles) of anhydrous HCl. Heat evolved during addition of HCl to MeOH. The flask was maintained at a temperature range from 20 to 25° C. by cooling and adjusting addition rate. Sodium toluene sulfinic acid (1.0 equivalents, 569 grams, 3.19 gmoles) was added and stired at room temperature for 1 to 4 hours. Water 2850 mls (5 volumes) was added, then and 2850 mls of toluene (5 volumes.) The mixture was stirred from 1 to 30 minutes and the layers were allowed to separate The layers were separated and the aqueous layer was back extracted twice using 1425 mls (2.5 volumes) of toluene for each back extraction. All toluene layers were combined and washed two times with 1425 mls (2.5 volumes) of 1 molar sodium bicarbonate solution for each wash. The layers were separated and the toluene layerers was concentrated under vacuum to approximately 3 volumes. The volumes were concentrated to a small alloquote to an oil on rotovap indicated a final weight yield of 476.78 grams of ester, 87.7% of theory weight.

Preparation 2

((2-ethyl-1-phenylmethyl)-1H-indol-4-yl)oxy) acetic acid methyl ester

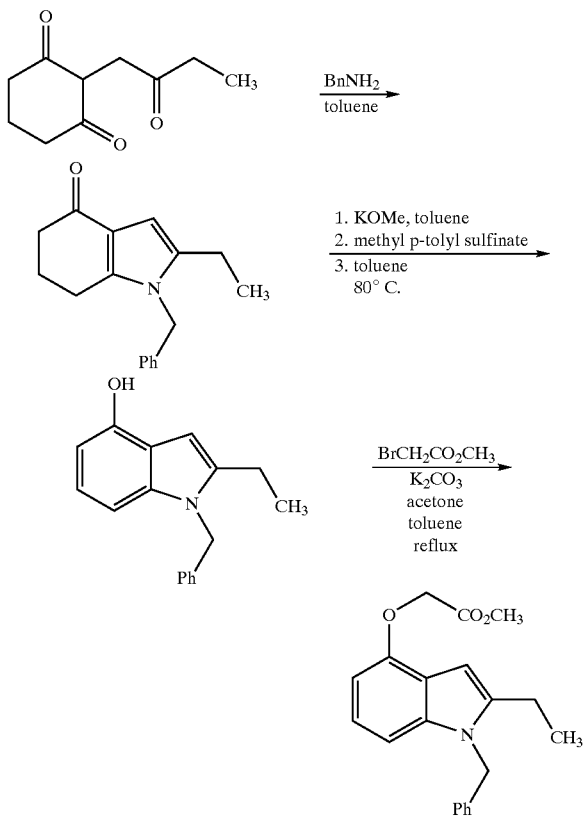

2-(2-oxobutyl)cyclohexane-1,3-dione (100 gms, 0.5 moles) was suspended in toluene (600 ml). The mixture was warmed to 85 deg C. and stirred for 5 minutes. Benzylamine (56.3 gms, 0.5 moles, 1.05 eq) was added dropwise over ~30–45 minutes. Following the addition the mixture turned to an amber colored solution. Heat was applied to the solution and water was azeotroped off until the reaction temperature reached 110 deg C. The reaction was allowed to stir at 110 deg C. for 1 hr at which time solvent was distilled off until 300 mL toluene remained. To this solution of 2-ethyl-1,5,6,7-tetrahydro-1-(phenylmethyl)-4H-indol-4-one was added a solution of methyl p-toluene sulfinate ester (127.5 g, 15 0.75 moles) in 300 mL toluene and potassium methoxide (110.5 g, 1.5 moles). The reaction mixture was stirred under nitrogen for 2 hrs with the reaction temperature between 30° C. and 40° C. TLC indicated complete consumption of starting material. The reaction was then cooled to 10° C. and quenched with water (500 mls). After stirring for 30 min, toluene (500 mls) was added and the layers were separated. The toluene solution of 2-ethyl-5-[4-methyl phenyl)sulfinyl]-1-benzyl-5,6,7-trihydroindole-4-one was heated at 80° C. for 2–3 hrs, at which time reaction completion was confirmed by TLC. The solution was cooled to room temperature. 250 mls MeOH and 312 mls 2 N NaOH was added and the mixture was stirred for 30 min. The layers were separated and the organic was extracted with 125 mls MeOH and 156 mls 2 N NaOH. The layers were separated and the aqueous layers were combined. Toluene (250 mls) was added to the aqueous layer and the pH of the aqueous was adjusted to 11 with 1 N HCl. The layers were separated and the organic layer was diluted with 1500 mls acetone. Powdered potassium carbonate (151.8 gms, 1.1 moles) and methylbromoacetate (93.6 gms, 0.6 moles) were added and the mixture was allowed to stir for 16 hrs at 60° C. The solids were filtered over polypropylene and washed with acetone (300 mls) A portion of the filtrate (60 g, or 5% of the total) was evaporated and the yellow solid was recrystallized from isopropyl alcohol (55 mls) to give title product as an off-white solid (6.5 g, 82% yield).

EXAMPLE 1

((2-Ethyl-1-(phenylmethyl)-1H-indol-4-yl)oxy) acetic Acid Methyl Ester

A. Preparation of 2-ethyl-1,5,6,7-tetrahydro-1-(phenylmethyl)-4H-indol-4-one 2-(2-oxobutyl)cyclohexane-1,3-dione (1000 gms, 4.995 moles) was suspended in toluene (6000 ml, 6 vol). The mixture was warmed to 85 deg C. and stirred for 5minutes. Benzylamine (562.6 gms, 5.25 moles, 1.05 eq) was added dropwise over ~30–45 minutes. Following the addition the mixture turned to an amber colored solution. Heat was applied to the solution and water was azeotroped off until the reaction temperature reached 110° C. The reaction was allowed to stir at 110° C. for 2 hrs at which time ~4000 mls of solvent was distilled off at atmospheric pressure. Solution was transferred to a flask and further evaporated to an amber viscous oil which was used directly in the following step.

Oil wt=1372.24 gms
Theoretical wt=1253.7 gms
Potency=87%
Molar yield=95.2%

B. Preparation of 2-Ethyl-(phenylmethyl)-1H-indol-4-ol

Sodium hydride (400 gms, 9.96 moles, 2.5 eq) was suspended in THF (5000 mls, 5vol). To the suspension was added the compound of part A, above, (1149 gms, 3.98 moles, 1 eq) and allowed to stir at 20–25 deg C. until bubbling had subsided. Methyl-p toluene sulfinate (1121 gms, 6.59 moles, 1.65 eq) was added and the mixture was heated to 30° C. After ~2.5 hrs, the mixture darkened as gas evolution and an exotherm to 47 deg C. was observed. TLC indicated complete consumption of starting material. The reaction was then cooled to 0 to 5° C. and quenched with the slow addition of deionized water (5000 mls, 5vol). The reaction was further quenched with glacial acetic acid (600 gms, 10 moles, 2.5 eq). The mixture was diluted with toluene (5000 mls, 5vol) and washed with saturated sodium bicarbonate (2500 mls, 2.5vol). The upper organic layer was washed with and additional 2500 mls of saturated sodium bicarbonate. The aqueous layers were combined and back extracted with toluene (5000 mls, 5vol). The organic layers were combined and heated to a gentle reflux (~80 deg C.) and stirred for 2 hours, at which time reaction completion was confirmed by TLC. The dark solution was concentrated atmospherically to ~4000 mls and washed with saturated sodium bicarbonate (1500 mls×2). The organic was dried over magnesium sulfate and was concentrated under vacuum to a dark viscous oil.

C. Preparation of ((2-ethyl-1-phenylmethyl)-1H-indol-4-yl) oxy) Acetic Acid Methyl ester.

A sample of the 2-ethyl-5-[(4-methylphenyl)sulfinyl]-1-benzyl 5,6,7-tihydroindol-4-one was purified by column chromatography with 50% ethyl acetate in hexane. Sulfoxide diastereomer with Rf 0.32 was isolated cleanly, and a mixture of sulfoxide diastereomers (Rf 0.32 and 0.26) was isolated. $^1$H and $^{13}$C NMR experiments were conducted on both samples:

TLC $R_f$ 0.32 (1/1 hexane/EtOAc). $^1$H NMR (CDCl$_3$, 300 MHz) δ 7.51 (dd, J=6.6, 1.6, 1H), 7.31–7.26 (m, 5H), 6.88 (d, J=6.4, 2H), 6.38 (d, J=8.1, 1H), 6.38 (t, J=1, 1H), 5.03 (s, 2H), 3.48–3.42 (m, 1H), 3.05–2.97 (m, 1H), 2.68–2.54 (m, 2H), 2.43–2.39 (m, 5H), 2.23–2.18 (m, 1H), 1.18 (t, J=7.5, 3H). $^{13}$C NMR (CDCl$_1$, 75 MHz) δ 185.53, 143.86, 141.41, 139.45, 138.25, 136.15, 129.67, 129.02, 127.71, 125.47, 124.76, 120.10, 102.43, 71.62, 47.14, 21.77, 21.48, 19.92, 19.35, 12.17. TLC $R_f$ 0.32 and 0.26 (1/1 hexane/EtOAc). $^1$H NMR (CDCl$_3$, 500 MHz, resonances distinguishable for $R_f$ 0.26) δ 6.82 (d, J=7.2, 2H), 6.33 (s, 1H), 4.94 (dd, J=16.9, 23.9, 2H), 4.01 (dd, J=4.7, 9.1, 1H). $^{13}$C NMR (CDCl$_3$, 75 MHz, all resonances observed) δ 186.98, 186.33, 144.82, 142.03, 140.06, 139.00, 137.58, 136.98, 136.85, 130.42, 130.11, 129.70, 129.65, 129.26, 128.37, 126.61, 126.27, 125.39, 120.91, 120.74, 103.04, 102.77, 71.97, 69.72, 61.01, 47.78, 47.12, 22.11, 21.90, 21.70, 21.30, 21.24, 20.68, 19.97, 19.71, 14.89, 12.84, 12.79.

D. Preparation of ((2-ethyl-1-(phenylmethyl)-1H-indol-4-yl)oxy)acetic Acid Methyl Ester

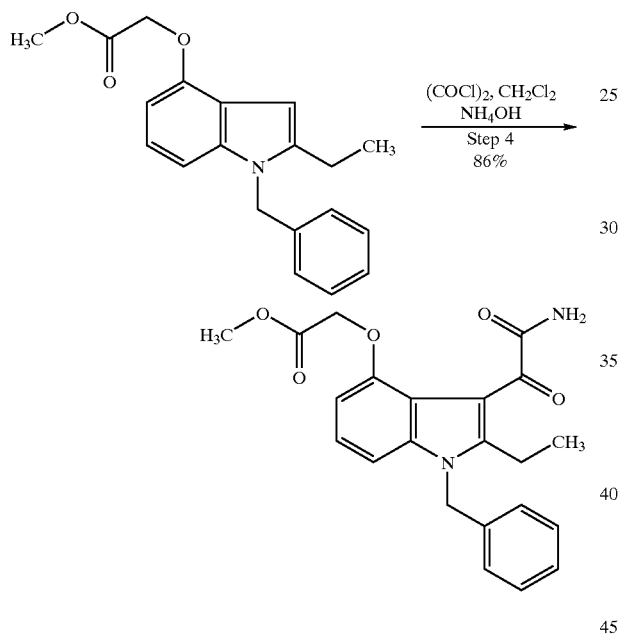

The compound of preparation 2 (25 g, 77 mmol) was dissolved in 175 mL dichloromethane and the solution was cooled with an ice bath. Oxalyl chloride (7.1 mL, 81 mmol) was added dropwise to maintain the reaction temperature below 35° C. After 30 min, a small amount of starting material was observed so additional oxalyl chloride (0.5 mL, 6 mmol) was added. After 30 min, the reaction was diluted with 175 mL dichloromethane and 175 mL water was added. Ammonium hydroxide (22 mL, 309 mmol)) was diluted with 75 mL water and cooled with an ice bath. The cold ammonia solution was added to the reaction mixture dropwise to maintain the reaction temperature below 6° C. At the end of the addition, the reaction mixture was warmed to 30° C. to dissolve all solids. After cooling to room temperature, the layers were separated and the organic layer was washed with water. The organic solution was mixed with 15 g activated carbon for 15 minutes. The mixture was filtered through Celite. The filtrate was evaporated to give a yellow solid which was recrystallized from 325 mL methanol to give the title product ((2-ethyl-1-(phenylmethyl)-1H-indol-4-yl)oxy)acetic acid methyl ester as a yellow solid (27.2 g, 89% yield).

What is claimed is:

1. An intermediate compound of the formula $V^1$

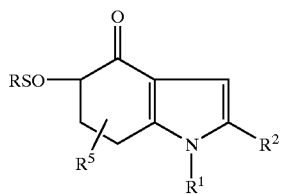

wherein:

R is selected from the group consisting of —(C$_1$–C$_6$) alkyl, aryl and substituted aryl R$^2$ is selected from the group consisting of C$_7$–C$_{20}$ alkyl;

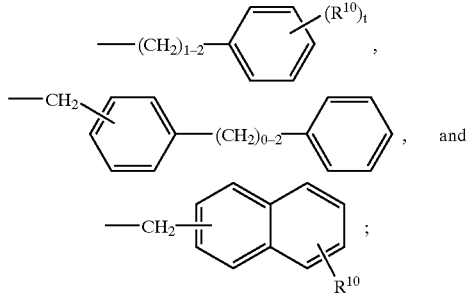

where;

R$^{10}$ is selected from the group consisting of halo, C$_1$–C$_{10}$ alkyl, C$_1$–C$_{10}$ alkoxy, —S—(C$_1$–C$_{10}$ alkyl) and halo (C$_{1-C10}$)alkyl, and t is an integer from 0 to 5 both inclusive;

R$^2$ is [selected from the group consisting of hydrogen, halo, C$_1$–C$_3$ alkyl, C$_3$–C$_4$ cycloalkyl, C$_3$–C$_4$ cycloalkenyl, —O—(C$_1$–C$_2$ alkyl), —S—(C$_1$–C$_2$ alkyl), aryl, aryloxy, and HET;] a heterocyclic group selected from the group consisting of thiazole, isothiazole, oxadiazole, and imidazole;

R$^5$ is selected from the group consisting of hydrogen, (C$_1$–C$_6$)alkyl, (C$_1$–C$_6$)alkoxy, halo(C$_1$–C$_6$)alkoxy, halo (C$_2$–C$_6$)alkyl, bromo, chloro, fluoro, iodo and aryl.

2. A compound of claim 1 wherein:

R is aryl;

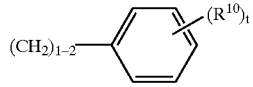

R$^1$ is

Where R$^{10}$ is selected from the group consisting of halo, —C$_3$–C$_{10}$ alkyl, —C$_1$–C$_{10}$(alkoxy), —S—(C$_1$–C$_{10}$)alkyl and halo (C$_1$–C$_{10}$)alkyl, and t is an integer from 0 to 5 both inclusive;

R$^2$ is a heterocyclic group selected from the group consisting of thiazole, isothiazole, oxadiazole, and imidazole;

R$^5$ is selected from the group consisting of hydrogen, —(C$_1$–C$_6$)alkyl and —(C$_1$–C$_6$)alkoxy.

3. A compound of claim 2 wherein R is phenyl or tolyl and R$^5$ is hydrogen.

* * * * *